United States Patent
Soane et al.

(10) Patent No.: US 6,951,712 B2
(45) Date of Patent: Oct. 4, 2005

(54) CRYOPROTECTIVE SYSTEM COMPRISING POLYMERIC NANO- OR MICRO-PARTICLES

(75) Inventors: David S. Soane, Piedmont, CA (US); Stephen E. Barry, Oakland, CA (US); Rachel Decor, El Cerrito, CA (US)

(73) Assignee: Alnis BioSciences, Inc.

( * ) Notice: Subject to any disclaimer, the term of this patent is extended or adjusted under 35 U.S.C. 154(b) by 462 days.

(21) Appl. No.: 10/221,381

(22) PCT Filed: Mar. 14, 2001

(86) PCT No.: PCT/US01/08522

§ 371 (c)(1), (2), (4) Date: Sep. 11, 2002

(87) PCT Pub. No.: WO01/67859

PCT Pub. Date: Sep. 20, 2001

(65) Prior Publication Data

US 2003/0044764 A1 Mar. 6, 2003

Related U.S. Application Data

(60) Provisional application No. 60/189,623, filed on Mar. 14, 2000.

(51) Int. Cl.[7] ................................................. A01N 1/00
(52) U.S. Cl. .......................................... 435/1.3; 435/1.2
(58) Field of Search ............................ 435/1.1, 1.2, 1.3

(56) References Cited

U.S. PATENT DOCUMENTS

| | | |
|---|---|---|
| 4,915,951 A | 4/1990 | Baldeschwieler et al. ... 424/450 |
| 4,938,961 A | 7/1990 | Collins et al. |
| 5,071,598 A | 12/1991 | Baldeschwieler et al. .... 264/4.3 |
| 5,336,616 A | 8/1994 | Livesey et al. .......... 435/240.2 |
| 5,405,742 A | 4/1995 | Taylor |
| 5,629,145 A | 5/1997 | Meryman ................... 435/1.3 |
| 5,750,330 A | 5/1998 | Tometsko et al. ............... 435/2 |
| 5,800,978 A | 9/1998 | Goodrich, Jr. et al. .......... 435/2 |
| 5,891,617 A | 4/1999 | Watson et al. ............... 435/1.3 |
| 5,958,670 A | 9/1999 | Goodrich, Jr. et al. .......... 435/2 |
| 5,969,052 A | 10/1999 | Shang et al. |
| 6,007,978 A | 12/1999 | Goodrich, Jr. et al. .......... 435/2 |
| 6,041,787 A | 3/2000 | Rubinsky .................... 128/898 |
| 6,176,089 B1 | 1/2001 | Bouche ......................... 62/64 |
| 6,410,645 B1 * | 6/2002 | Pathak et al. ............... 424/78.2 |
| 6,451,346 B1 * | 9/2002 | Shah et al. ................. 424/486 |

FOREIGN PATENT DOCUMENTS

| | | |
|---|---|---|
| EP | 0 693 508 | 1/1996 |

OTHER PUBLICATIONS

Topp, M.D.C. et al., "Thermosensitive Micelle–Forming Block Copolymers of Poly(ethylene glycol) and Poly(N–isopropylacrylamide)", *Macromolecules, ACS*, vol. 30, No. 26, Dec. 29, 1997, pp 8518–8520.

Horak, D. et al., "Hydrogels in Endovascular Embolization I. Spherical Particles of Poly-2-Hydroxyethyl Methacrylate and Their Medico-Biological Properties", *Biomaterials*, vol. 7, No. 3, 1986, pp 188–192.

* cited by examiner

*Primary Examiner*—Sandra E. Saucier
(74) *Attorney, Agent, or Firm*—Jacqueline S. Larson

(57) ABSTRACT

The present invention is directed to a cryoprotective system that comprises an aqueous solution containing polymeric nano- and micro-particles that exhibit a reversible temperature-dependent volume change. It is also directed to a method for providing cryoprotection to an organism or parts of an organism by pumping the cryoprotective system into the vasculature of the organism prior to exposing the organism to a lower, preferably below 0° C., temperature.

14 Claims, No Drawings

CRYOPROTECTIVE SYSTEM COMPRISING POLYMERIC NANO- OR MICRO-PARTICLES

This application is a U.S. National Stage application of International Patent Application PCT/US01/08522, filed on Mar. 14, 2001, which claims the benefit of U.S. Provisional Patent Application No. 60/189,623, filed on Mar. 14, 2000, the entire disclosure of which is incorporated herein by reference.

TECHNICAL FIELD

This invention relates to the cryoprotection of tissues, organs, and organisms. More particularly, the present invention relates the use of thermally reversible controlled polymer nano- and microparticles for cryoprotective applications.

BACKGROUND OF THE INVENTION

The ability to lower the temperature of organs, tissues or a whole organism without causing extensive damage is of the highest interest for both preservation and transplantation applications as well as for the development of hypothermic surgery. In the first case, lowering the temperature as much as possible is important to extend the storage time between organ harvesting and transplantation. But so far, the lack of adequate cryoprotection systems for tissues and organs has prevented lowering the temperature of organs to below freezing temperatures during organ transportation and storage. Such temperatures damage the tissue, especially the fragile vasculature of the organs such as the lungs, the liver or the heart. (http://www.britannica article: "Transplant", sub-section: "organ and tissue banks").

The damage done to the cells and vasculature of tissues upon freezing is the result of two deleterious processes: osmotic stress caused by an increase in solute concentration when ice crystals form, and the physical damage (i.e. cellular rupture and vascular puncturing) caused by ice crystal growth. (Belzer F. O., Southard J. H., Principles of solid-organ preservation by cold storage. *Transplantation.* 1988, 45, 673–676)

In the same way, the development of hypothermic surgery for operations of the heart or the brain has been hindered by the lack of adequate cryoprotective blood replacement liquid that would allow a surgeon to intervene for a longer time on a body in a state of blood flow interruption and reduced metabolism.

A greater degree of cryoprotection of tissue vasculature has been accomplished through blood substitutes containing various solutes. For example, small molecules such as glycerol and DMSO have been employed. These solutes beneficially penetrate cells and provide intra- and extracellular protection, but their concentrations are limited due to toxicity. Polymers such as substituted starches, dextran, and polyethylene glycol have also been employed. See, e.g., U.S. Pat. Nos. 5,405,742 and 4,938,961. These materials do not penetrate the cell, but can beneficially decrease the freezing point of the physiological liquids and additionally may limit crystal formation and growth in the vasculature. However, the polymer concentrations necessary to substantially reduce crystal growth tend to possess an unacceptably high viscosity (which makes it very difficult to pump into small vasculature). Antifreeze proteins from organisms, which live in sub-freezing temperatures, have also been explored as cryoprotective solutions. Particles of poly(2-hydroxyethyl methacrylate) have been used for endovascular embolization, but use for cryoprotection was not disclosed (Horak, et al., *Biomaterials,* 1986, 7:188–190).

A low-toxicity solution that optimally protects vasculature and organs against ice crystal growth and osmotic stress has yet to be achieved.

SUMMARY OF THE INVENTION

The present invention is directed to controlled thermally-reversible polymer nano- and microparticles and their use for cryoprotective applications. More specifically, this invention is directed to a cryoprotective system comprising an aqueous solution containing polymeric particles that exhibit a reversible temperature-dependent volume change ("particle solution"). In an appropriate aqueous solution, the particles possess the property of swelling as the temperature is decreased. The particles may range in size, in their fully swollen state, from about 10 to about 10,000 nm, preferably from about 100 to about 1000 nm.

When blood vessels are filled with the particle solution of the invention, the tissue vasculature is protected when the tissue is significantly cooled or even frozen. While not wishing to be bound by theory, it is believed that the particles function mostly by confining ice crystal growth in blood vessels. Thus, this invention is further directed to a method of providing cryoprotection to an organism or parts of an organism such as organs or tissue samples. In the first step of the method, the particle solution is pumped into the vasculature of the organism at a temperature where the particles are in their unswollen state, thus allowing them to freely flow through the finest capillaries. Upon exposure of the system to lowered temperatures, such as near 0° C., the polymer spheres expand and substantially fill the volume of the vessel.

The cryoprotective system also optionally contains a beneficial solute or solutes, which are thermodynamically or mechanically excluded from the polymer sphere's core. In one embodiment of the invention, the beneficial solute concentration in the interfacial fluid is high enough to reduce the freezing point to below the temperature to which the tissue will be exposed.

At the end of the low temperature phase, the tissues, organs, or entire body is heated, causing the polymer spheres to shrink. This reversibility of the temperature-sensitive physical modifications allows an easy removal of the particles in their unswollen state.

DETAILED DESCRIPTION OF THE INVENTION

The terms "a" and "an" mean "one or more" when used herein and in the appended claims.

By "cryoprotective" is meant the ability to protect an organism or part of an organism such that when the organism is frozen or otherwise exposed to a lower, normally destructive, temperature, no extensive damage is done to the organism and especially to the cells and, if present, to the vasculature of the tissues The term "organism" as used herein and in the appended claims refers generally to living organs, tissues, cells, or a whole organism, whether plant or animal, unless otherwise indicated.

The use of particles that expand as they are cooled accomplishes at least two things. First, it allows the particle solution to be pumped into the vasculature at low viscosity when the solution and the vasculature are at relatively high temperatures (e.g., at or near body temperature). Because of the high viscosity of a high concentration of swollen polymer spheres, the particles cannot, as a practical matter, be put in place in their expanded state. The particles are thus composed of a polymer network that expels water and thus shrinks as the temperature is raised, and swells with water and thus expands as the temperature is lowered. At temperatures above the critical solution temperature, the polymer spheres are in a contracted, water-depleted state. In this state, the viscosity of the cryoprotective solution containing the polymer particles is low and the solution can be easily pumped into the vasculature. When the temperature is cooled, the particles swell with water and expand. The temperature at which the physical properties of the material undergo a transition is called lower critical solution temperature (LCST).

Second, the volume increase of the particles upon their expansion when the solution is cooled results in a decrease in the volume external to the particles. When the particles are used at a high enough concentration, they impinge upon one another in their swollen state. The expansion thus "squeezes" the optional beneficial solutes in the cryoprotective system into the space between the particles, provided that the solutes do not enter the particles upon expansion. It is expected that most of the beneficial solutes above a given size will be kept outside the particles due to the gel network and/or the chemical or physical characteristics of the solute. This large local concentration of beneficial solute between the swollen particles may lower the freezing point of the interface zone to below that to which the tissue is exposed, and thus prevent ice crystal growth in the interfacial region. Special solutes such as antifreeze proteins added to the cryoprotective solution may further improve performance.

The particles should undergo expansion below the body temperature of the organism. In one embodiment, expansion occurs at sub-ambient temperatures, but above the freezing temperature of pure water; that is, between 1° C. and 20° C. In one embodiment of the invention, the particles consist of a polymer that displays a Lower Consolute Solution Temperature (LCST). Although the expansion is greatest at the transition (LCST) temperature, the polymer particles continue to expand below the transition temperature as the temperature is lowered. Thus, a polymer that has a transition temperature higher than the temperature to which the polymer will be exposed in application may be advantageously employed in the invention.

Polymer particles have an undesirable tendency to aggregate. In their hydrophobic, shrunken state above the transition temperature, aggregation may be avoided by functionalizing the particles with elements limiting this aggregation. Such elements can be selected from, for example, polyethylene glycol, hydroxyethylstarch or polyglycosides chains, but are not limited thereto.

The average size of the polymer particles in their fully water-swollen state should preferably range from about 10 to about 10,000 nm, more preferably from about 100 to about 1000 nm. While not wishing to be bound by theory, it is believed that smaller average sizes than 100 nm may not be as desirable because they will have a greater osmotic pressure per unit weight of polymer than the larger polymers. This larger osmotic pressure can deleteriously result in dehydration of the endothelial cells beyond a desired level. However, some cellular dehydration may be desirable to reduce the damage of ice crystals growing in the interior of the endothelial cells. It is believed that larger average size than 1000 nm may not be desirable because the mass transfer of water into the particles may be slower than what is practical.

The invention provides for the replacement of blood, including the red blood cells, by the cryoprotective particles solution prior to reducing the temperature to temperatures, such as sub-zero temperatures, that would be harmful in the absence of cryoprotectants.

Nanoparticle Composition and Method of Formation

There are many aqueous polymer solutions documented in the scientific literature that display LCST behavior (A. P. Assi et al., *Electrophoresis*, 1996, 17, 1460–1469; M. D. C. Topp et al., *Macromolecules*, 1997, 30, 8518–8520; U.S. Pat. Nos. 5,969,052; 5,162,582; Japan Kokai tokkyo koho 95331224; International pat. applications WO 95/21876 and WO 98/29461). These systems are explained in detail in "Responsive Gels: Volume Transitions I and II", K. Dusek, ed., *Advances in Polymer Science*, Vols. 109 and 110, Springer-Verlag, 1993, herein incorporated by reference. One way of forming LCST polymers is by free-radical polymerization of substituted acrylamides or methacrylamides such as N-isopropyl acrylamide (NIPA) and acrylated compounds such as hydroxyethylacrylate. In order to form crosslinked networks as opposed to linear monomers, appropriate multifunctional monomers must be included in the formulation prior to polymerization. Examples of possible crosslinkers include methylene bisacrylamide, acetic acid bisacrylamide, and ethylene glycol diacrylate. An example monomer formulation is 98 wt % NIPA and 2 wt % MBA. Poly-NIPA is known to have a transition temperature of 32° C. in water. For a given monomer, the transition temperature of the gel formed can also be tuned according to the chemical nature and quantity of crosslinker used, which methods are known in the art and can be determined without undue experimentation. Particles of N-isopropyl acrylamide crosslinked with methylene bisacrylamide have been shown to expand to 100 times the contracted-state volume. Using more hydrophobically-substituted acrylamides may lower the transition temperature. However, the transition volume change is concomitantly reduced as polymer hydrophobicity increases, thus reducing the change in viscosity.

To exhibit the desired LCST, the reversible temperature-sensitive polymer particles of the present invention can be composed from polymer mixtures or copolymers capable of giving an appropriate temperature response. These polymers may be selected from, but are not limited to, acrylamides, methacrylamides and their derivatives; polyethylene glycols, di-acrylates and hydroxyethylmethacrylates; octyl/decyl acrylates; acrylated aromatic and urethane oligomers; vinylsilicones and silicone acrylates; polypropylene glycols; polyvinylmethyl ethers; polyvinylethyl ethers; polyvinyl alcohols; polyvinyl acetates; polyvinyl pyrrolidones; polyhydroxypropyl acrylates; ethylene, acrylates and methacrylates; N-acryloylpiperidines; N-acryloylpyrrolidines; nonyl phenols; cellulose; methyl cellulose; hydroxyethyl cellulose; hydroxypropyl methyl cellulose; hydroxypropyl cellulose; ethyl hydroxyethyl cellulose; hydrophobically-modified celluloses; dextran; hydrophobically-modified dextrans; agarose; low-gelling-temperature agaroses; and copolymers thereof.

The polymer particles may be formed through reverse emulsion polymerization, suspension polymerization, dispersion polymerization (C. K. Ober, K. P. Lok, M. L. Hair, Journal of Polymer Sciences, Polymer Letters Ed., vol 23, 103–108, 1985), or precipitation polymerization techniques (Arshady, R., Colloid Polym. Sci., 1992, 270, 717–732). For example, reverse emulsions are capable of producing nanoparticles ranging in size from 0.1 nm to 1000 nm in the expanded state. U.S. Pat. Nos. 5,286,806 and 5,530,069 describe the preparation of hydrolyzed polyacrylamides from reverse emulsions. As the nanoparticles of the invention preferably have diameters on the order of the diameters of red blood cells or smaller, the previously mentioned size ranges, accessible via reverse emulsion polymerization and dispersion polymerization, are appropriate.

Preferentially, the particles are formed via a dispersion polymerization method at temperatures above the LCST. The monomers are soluble in the aqueous solution at the elevated reaction temperature (e.g. 80° C.), but the polymer formed is above the LCST and is thus insoluble. In order to obtain a fairly monodisperse sample containing nano- or micro-particles, a polymeric surfactant such as PVP, PVA, hydroxyethylene starch, or other starch derivatives can be included in the reaction mixture (Y. Almoy, S Reich, M Levy, British Polym. J., 14, 131 (1982)). The surfactant also "encapsulates" the growing particles and thus keeps them separated from one another. Increasing the surfactant concentration reduces the particle size. Particle size can be varied from 100 to 100,000 nm using this technique.

Preparation of Nanoparticles

A mixture of water-soluble monomers containing reactive functionalities, a crosslinker containing at least two reactive functional groups per molecule, and a thermo- or photoinitiator are dissolved in water in the following proportions:

Monomers: 0.5 to 30 wt %, preferentially 1 to 2 wt % of the total mixture.

Crosslinker: 0.1 to 20 wt %, preferentially 1 to 2 wt % of the monomer.

Thermo- or photoinitiator: 0.05 to 2 wt %, preferentially 1 wt % of the monomer and crosslinker mixture.

A polymer coemulsifier is dissolved in the aqueous solution, to be used as a stabilizer. The solution is degassed before polymerization and heated under vigorous stirring between 70° C. and 95° C. After 2 hours to 10 hours, the reaction is completed and can be cooled down.

If necessary, the resulting particles can be separated from the polymeric coemulsifier through dialysis, ultrafiltration, centrifugation, fractionated precipitation, or any other technique known to one of ordinary skill in the art.

Alternatively, the use of non water-soluble compounds is made possible by replacing totally or in part the reaction media by more lipophilic solvents such as alcohols.

Where the reactive functional groups are acrylamide functionalities, monomers can be selected from those consisting of, but not limited to, N-acryloylpiperidine, diacetoneacrylamide, N-methylacrylamide, N-ethylacrylamide, N-n-propylmethacryl-amide, N-butylacrylamide, N-isopropylacrylamide, N-isopropylmethacrylamide, N-cyclopropylacrylamide, N-cyclopropylmethacrylamide, N-acryloylpyrrolidine, N,N-diethylacrylamide, N,N-ethylmethylacrylamide, and N-ethoxymethylacrylamide.

Exemplary crosslinkable groups include, but are not limited to, acrylate, acrylamide, vinyl ether, styryl, epoxide, maleic acid derivative, diene, substituted diene, thiol, alcohol, amine, hydroxyamine, carboxylic acid, carboxylic anhydride, carboxylic acid halide, aldehyde, ketone, isocyanate, succinimide, carboxylic acid hydrazide, glycidyl ether, siloxane, alkoxysilane, alkyne, azide, 2'-pyridyldithiol, phenylglyoxal, iodo, maleimide, imidoester, dibromopropionate, and iodacetyl. Crosslinkers having acrylamide functional groups may be selected from, but are not limited to, methylenebisacrylamide, bisacrylamidoacetate, N,N'-(1,2-dihydroxy-ethylene) bisacrylamide, and N,N'-bisacrylcystamine.

Initiators may be selected from, but are not limited to, potassium persulfate and 4,4'-azobis(4-cyanovaleric acid).

Polymeric coemulsifiers or stabilizers may be selected from, but not limited to, polyvinylalcohol, polyvinylpyrrolidone, hydroxyethylstarch, polyethylene sorbitan monoalkyl derivatives (Tween™), sodium 1,2-methylenebis(2-ethylhexyloxy-carbonyl)ethanesulfonate (AOT), Triton™, and octanoic acid.

Post-synthesis Functionalization of the Particles

The surface of the previously described particles can be further functionalized after the polymerization step. Such functionalizations can provide desired enhancements, such as, but not limited to modifications to physical properties (for example, LCST variation, viscosity, hydrophilicity, miscibility, flocculation, or suspendability), enhanced cryoprotection, biocompatibility, or the possibility to follow the injection and removal of the product from the organism.

Functionalizations can consist of, but are not limited to, the attachment of polyethyleneglycol chains, peptides or proteins, fluorescent or colorimetric dyes, or radio-opaque or radiolabelled compounds, and can be attached either directly or via a tether arm to the particle's surface.

The functionalization consists of the attachment of functional groups or molecules such as the above to the surface of the particles by a coupling between a set of reactive functions: The ones at the surface of the particles originate from reactive functions bearing monomers or crosslinkers and react with complementary reactive functions borne by the said molecule either directly or on a tether.

Several combinations of reactive moieties, preferentially belonging to a pair of chemoselective reagents (such as, for example, amines+acids, thiol+sulfhydryls, ketones+aminooxys, and the like), are available to one skilled in the art (see for example Lemieux, G., Bertozzi, C., *Trends in Biotechnology*, 1998, 16, 503–513).

Preparation of the Cyroprotective System

The cryoprotective system is prepared by suspending the polymeric particles of the invention in a physiologically acceptable solution at a temperature above the critical solution temperature of the particles, and conveniently at room temperature. The particles will be present in the solution in an amount of from about 0.5 wt % to about 35 wt %, preferably from about 2 wt % to about 10 wt %. As long as the solution is kept above the critical solution temperature, the particles will be in their non-swollen state.

Examples of appropriate solutions include, but are not limited to, pure water, hetastarch, physiological buffers or any liquid that is at least partially compatible with the physiology of the organism to be preserved. An example fluid is the commercially available blood volume expander Hextend™ (distributed by Abbott Labs). Hextend is composed of 6 wt % of the macromolecule hydroxyethylstarch, 0.099 wt % of dextrose and a mixture of salt and buffer components (NaCl 0.672 wt %; $CaCl_2$, $2H_2O$ 0.037 wt %; KCl 0.022 wt %; $MgCl_2$, $6H_2O$ 0.009 wt %), including sodium lactate (0.317 wt %). Because the addition of the particles will raise the solution osmolarity somewhat, it may be desirable to use less than 6 wt % hydroxyethyl starch. This can be determined for the target organism by methods known in the art without undue experimentation.

The cryoprotective solution may further optionally include one or more "beneficial solutes" that may be thermodynamically or mechanically excluded from the polymer particle's core. The beneficial solute may decrease the freezing point of the physiological liquids to below the temperature at which the organism will be exposed and/or it may limit ice crystal formation and growth in the vasculature. At higher osmolarity, it can also dehydrate cells to a beneficial extent. Because the expansion of the polymeric particles reduces the volume of fluid in the treated vasculature, the amount of beneficial solute necessary to be efficacious is low enough to be non-toxic to the surrounding cells. Beneficial solutes useful in the present invention include, but are not limited to, glycerol, DMSO, substituted starches, dextran, and polyethylene glycol. The solute or mixture of solutes is present in the final cyroprotective system in an amount of from 0 wt % to about 30 wt %, preferably from about 2 wt % to about 10 wt %.

The cryoprotective system of the invention is useful in protecting an organism without causing extensive damage to the organism at low temperatures, such as freezing, that normally would cause such damage. The damage done to the cells and vasculature of tissues upon freezing is the result of two deleterious processes: osmotic stress caused by an increase in solute concentration when ice crystals form, and the physical damage (e.g., cellular rupture and vascular puncturing) caused by ice crystal growth. The ability to maintain a healthy organism at low temperatures is valuable for the preservation of the organism. Thus, for example, organs, parts of organs (such as liver lobes, small bowel parts or pancreatic islets) or connected groups of organs (such as the ensemble of lungs and heart) for transplant can be stored for an extended period of time until a transplant recipient becomes available. The ability for an organ to be safely transported from one location to another is greatly increased. Additionally, extended time of storage for an organ or tissue intended for grafting allows more time to check that it is matched with the donor (size, blood group, HLA, etc.) and develop the tests necessary to prevent the transmission of diseases (for example malaria parasites, viral infections such as HIV or Hepatitis C, Creutzfeld-Jacob prions, and the like). Finally, the capacity to better preserve organisms near or below 0° C. could allow the harvesting of organs or tissues from deceased donors which are currently rejected for having suffered a warm ischemia.

Other organisms (such as blood vessels; heart valves; umbilical cords; tissue samples such as cornea, derm and epidermis; intact spinal cord; bone marrow samples; prostate, stomach or bladder tissues; sperm; eggs; seeds; cells; or vegetal meristem) may also be safely stored for extended periods and remain viable. The system may further be used as a blood replacement liquid in hypothermic surgery, allowing a longer intervention by the surgeon.

EXAMPLES

The following examples are provided to illustrate the practice of the present invention, and are intended neither to define nor to limit the scope of the invention in any manner.

Example 1

Nanoparticle Fabrication

N-isopropylacrylamide (2.72 g), methylene-bis-acrylamide (0.540 g), 4,4'-azobis(4-cyanovaleric acid) (0.030 g), and 0.635 g of polyvinylpyrrolidone (55,000 average molecular weight) are dissolved in 220 mL of distilled water. The solution is degassed with stirring under the vacuum of a water-pump aspirator for three times 20 minutes and flushed in between with nitrogen. The mixture is heated at 90° C. for 2 hours.

The resulting white solution is allowed to cool. It can be used as such, or it can be dialyzed against distilled water in a 200,000 Da cut-off dialysis membrane bag for 12 hours. The remaining suspension can be lyophilized to give pure poly-N-isopropylacrylamide beads or particles of narrow polydispersity of a 1.2 μm average diameter.

Alternatively, the solution can be ultrafiltrated through membranes of different porosity. Filtration through a membrane of 500,000 average molecular weight cut-off allows partial or nearly total removal of PVP from the solution. Sterile particle solutions or dry particles can be stored for an extended period of time without damage.

Example 2

Nanoparticle and Cryoprotective Solution Fabrication

N-isopropylacrylamide (2.72 g), methylene-bis-acrylamide (0.540 g), and 4,4'-azobis(4-cyanovaleric acid) (0.030 g) are dissolved in a starch-containing buffer. A broad scope of buffers and starch derivatives and concentrations thereof can be used. In one synthesis, the reaction was performed in 220 mL of buffer containing, for 100 mL:

| | |
|---|---|
| NaCl | 672.0 mg |
| Hydroxyethylstarch | 300.7 mg |
| Sodium lactate | 312.0 mg |
| $CaCl_2$ | 27.9 mg |
| KCl | 22.0 mg |
| $MgCl, 6H_2O$ | 9.0 mg |
| Dextrose | 4.5 mg |

The solution is degassed with stirring under the vacuum of a water-pump aspirator for three times 20 minutes and flushed in between with nitrogen. The mixture is heated at 90° C. for 2 hours. The white solution is allowed to cool and can be used directly as the cryoprotective solution, or the particles may be isolated and stored for later use using methods such as described in Example 1 or otherwise known in the art.

Example 3

Nanoparticle and Cryoprotective Solution Fabrication

N-isopropylacrylamide (2.00 g), diacetoneacrylamide (0.80 g), methylene-bis-acrylamide (0.54 g), and 4,4'-azobis (4-cyanovaleric acid) (0.030 g) are dissolved in a starch-containing buffer. The solution is degassed with stirring with three freeze-pump-thaw cycles: (one freeze-pump-thaw cycle=the mixture, in a closed vial, is frozen by placing it in a liquid nitrogen bath, the mixture is put under high vacuum for 20 min, the vacuum is stopped, and the solution is allowed to warm up to room temperature). The mixture is then flushed with nitrogen and heated at 90° C. for 2 hours. The solution is allowed to cool and can be used directly as the cryoprotective solution, or the particles may be isolated and stored using methods such as described in Example 1 or otherwise known in the art.

Example 4

Particles synthesized with a monomer mixture containing diacetoneacrylamide are suspended in an aqueous buffer and allowed to react with an excess of mono-amino-oxy-polyethylene glycol. The particles are purified by techniques known to those skilled in the art, such as FPLC or centrifugation, to afford PEG-functionalized nanoparticles with a defined LCST.

Example 5

Dry, lyophilized poly-N-isopropylacrylamide particles (50 mg), prepared as in Example 1, are suspended in 561 mL of buffer and left from 1 to 12 hours, until they reach the maximum hydration state corresponding to the temperature at which they are placed.

Example 6

The polymer particle-containing solution synthesized with the procedure described in Example 2 can be used as such. The polymer particles can also be very easily transferred in any desirable buffer with the following method: The suspension is incubated with amylase (which decomposes the starch derivatives) and dialyzed against water and/or the desired buffer.

Suspensions have been prepared in aqueous phases such as the following ones:
Pure water
Hetastarch
Physiological buffers of the following composition:

|  | For 100 mL: |
|---|---|
| Buffer A: | |
| NaCl | 672 mg |
| Sodium lactate | 312 mg |
| $CaCl_2$, $2H_2O$ | 37 mg |
| KCl | 22 mg |
| $MgCl$, $6H_2O$ | 9 mg |
| Buffer B: | |
| NaCl | 689.5 mg |
| $CaCl_2$ | 27.9 mg |

The above suspensions are transparent liquids at room temperature but thicken when the temperature decreases. The swelling of the particles can be monitored by measuring the changes of the solution's viscosity. At −7° C., the solutions are still not frozen but appear to be like viscous slurries.

The temperature depression of the freezing point compared to water depends on the concentration of the particles and the composition of the buffer used, and can be manipulated by one of ordinary skill in the art without undue experimentation.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention.

What is claimed is:

1. A method of providing cryoprotection to an organism, the method comprising:
    pumping a cryoprotective aqueous solution into the vasculature of said organism, said cryoprotective aqueous solution comprising polymeric nano- or micro-particles that exhibit a reversible temperature-dependent volume change and wherein said polymeric particles are in their non-swollen state; and
    exposing said organism to a lowered treatment temperature, causing said polymeric particles to be in their swollen state.

2. The method according to claim 1 wherein said cryoprotective aqueous solution further comprises a beneficial solute.

3. The method according to claim 2 wherein said beneficial solute is selected from the group consisting of glycerol, DMSO, substituted starches, dextran, and polyethylene glycol.

4. The method according to claim 1 wherein said polymeric particles comprise a polymer selected from the group consisting of acrylamides, methacrylamides and their derivatives; polyethylene glycols, di-acrylates and hydroxyethylmethacrylates; octyl/decyl acrylates; acrylated aromatic and urethane oligomers; vinylsilicones and silicone acrylates; polypropylene glycols; polyvinylmethyl ethers; polyvinylethyl ethers; polyvinyl alcohols; polyvinyl acetates; polyvinyl pyrrolidones; polyhydroxypropyl acrylates; ethylene, acrylates and methacrylates; N-acryloylpiperidines; N-acryloylpyrrolidines; nonyl phenols; cellulose; methyl cellulose; hydroxyethyl cellulose; hydroxypropyl methyl cellulose; hydroxypropyl cellulose; ethyl hydroxyethyl cellulose; hydrophobically-modified celluloses; dextran; hydrophobically-modified dextrans; agarose; low-gelling-temperature agaroses; and mixtures thereof; and copolymers thereof.

5. The method according to claim 1 wherein said lowered treatment temperature is below the body temperature of said organism.

6. The method according to claim 1 wherein said polymeric particles have a lower critical solution temperature higher than said lowered treatment temperature.

7. The method according to claim 1 which comprises the further steps of exposing said organism to a temperature above the lower critical solution temperature of said polymeric particles, causing said swollen polymeric particles to return to their non-swollen state; and removing said polymeric particles from said organism.

8. The method according to claim 1 wherein said cryoprotection is for transport or storage of said organism.

9. The method according to claim 1 wherein said organism is other than a human or animal body.

10. The method according to claim 1 wherein said organism is an organ.

11. The method according to claim 1 wherein said organism is a tissue sample.

12. The method according to claim 1 wherein said organism is a plant or a part of a plant.

13. The method according to claim 1 wherein the surface of said polymeric particles are functionalized with one or more functional groups or molecules that provide a desired enhancement.

14. The method according to claim 13 wherein the functional groups or molecules are selected from the group consisting of polyethyleneglycol chains, hydroxyethylstarch chains, polyglycoside chains, peptides, proteins, fluorescent dyes, colorimetric dyes, radio-opaque compounds, and radiolabelled compounds.

* * * * *